(12) United States Patent
Oniki et al.

(10) Patent No.: US 7,648,363 B2
(45) Date of Patent: Jan. 19, 2010

(54) METHOD OF WHITENING TEETH, TOOTH WHITENING COMPOSITION AND TOOTH WHITENING SET

(75) Inventors: Takayuki Oniki, Tokyo (JP); Takashi Watanabe, Tokyo (JP); Akira Uchiyama, Tokyo (JP)

(73) Assignee: Lion Corporation, Tokyo (JP)

( * ) Notice: Subject to any disclaimer, the term of this patent is extended or adjusted under 35 U.S.C. 154(b) by 421 days.

(21) Appl. No.: 10/491,191

(22) PCT Filed: Sep. 30, 2002

(86) PCT No.: PCT/JP02/10150

§ 371 (c)(1),
(2), (4) Date: Mar. 31, 2004

(87) PCT Pub. No.: WO03/030851

PCT Pub. Date: Apr. 17, 2003

(65) Prior Publication Data

US 2004/0219112 A1    Nov. 4, 2004

(30) Foreign Application Priority Data

Oct. 1, 2001    (JP) .............................. 2001-305133

(51) Int. Cl.
*A61C 5/00*    (2006.01)
(52) U.S. Cl. ........................ 433/215; 424/49
(58) Field of Classification Search ................ 433/215, 433/216, 222.1; 424/49–58, 401
See application file for complete search history.

(56) References Cited

U.S. PATENT DOCUMENTS

| 4,032,627 A | | 6/1977 | Suchan et al. |
| 4,117,109 A | * | 9/1978 | Stookey ........................ 424/57 |
| 5,409,631 A | * | 4/1995 | Fischer ................... 252/186.25 |
| 5,454,719 A | * | 10/1995 | Hamblen .................... 433/215 |
| 5,631,000 A | * | 5/1997 | Pellico et al. ................. 424/53 |
| 5,645,821 A | * | 7/1997 | Libin ........................... 424/49 |
| 5,718,886 A | | 2/1998 | Pellico |
| 5,739,177 A | | 4/1998 | Ohno et al. |
| 5,891,453 A | | 4/1999 | Sagel et al. |
| 5,944,528 A | * | 8/1999 | Montgomery ............... 433/215 |
| 6,312,671 B1 | * | 11/2001 | Jensen et al. ................... 424/53 |
| 6,475,469 B1 | * | 11/2002 | Montgomery ................ 424/49 |
| 6,479,037 B1 | * | 11/2002 | Montgomery ................ 424/53 |
| 6,610,276 B2 | * | 8/2003 | Melman ....................... 424/57 |
| 2004/0033205 A1 | * | 2/2004 | Date et al. .................... 424/53 |

FOREIGN PATENT DOCUMENTS

| JP | 4-82821 A | 3/1992 |
| JP | 5-5884 A | 3/1993 |
| JP | 7-187941 A | 7/1995 |
| JP | 7-187942 A | 7/1995 |
| JP | 9-100215 A | 4/1997 |
| JP | 9-151123 A | 6/1997 |
| JP | 9-202718 A | 8/1997 |
| JP | 2000-72636 A | 3/2000 |
| JP | 2000-281548 A | 10/2000 |
| JP | 2001-278761 A | 10/2001 |
| JP | 2002-193775 A | 7/2002 |
| WO | WO 91/14650 A1 | 10/1991 |
| WO | WO 95/17158 A1 | 6/1995 |
| WO | WO-98/55044 A1 | 12/1998 |
| WO | WO 01/54610 A1 | 8/2001 |

OTHER PUBLICATIONS

Chemical Abstracts, vol. 132, No. 15, Columbus, Ohio, US abstract No. 198896, XP002387782, (Apr. 3, 2000).

* cited by examiner

*Primary Examiner*—Cris L Rodriguez
*Assistant Examiner*—Hao D Mai
(74) *Attorney, Agent, or Firm*—Birch, Stewart, Kolasch & Birch, LLP

(57) ABSTRACT

A method of reversibly whitening teeth in the presence of water which comprises allowing a tooth whitening component to infiltrate into the enamel surface layer toward the inside and remain therein so as to make the enamel cloudy and white by altering its optical properties without causing any chemical reactions, thereby whiten the thus treated teeth compared with untreated ones.

20 Claims, No Drawings

METHOD OF WHITENING TEETH, TOOTH WHITENING COMPOSITION AND TOOTH WHITENING SET

TECHNICAL FIELD

The present invention relates to a new method for making teeth look whiter than original and, more particularly, to a method for making teeth apparently look white. The method includes causing a whitening component to infiltrate into the tooth enamel so that the whitening component replaces water in the enamel, thereby changing the optical properties (refractive index, reflectance, and the like) of the enamel without chemical reactions such as bleaching. The present invention relates also to a tooth whitening composition and a tooth whitening set.

BACKGROUND ART

Several procedures have been employed to make teeth look white. They are divided into two categories.
(1) One which is intended to remove stains adhering teeth, thereby making teeth look as white as original.
(2) One which is intended to make teeth look whiter than original.

The first procedure includes physical ones such as brushing with a toothbrush and a dentifrice containing an abrasive, and chemical ones such as decomposition of stains with a solubilizer (e.g., ethylene glycol and polyvinyl pyrrolidone), enzyme, chelating agent, or the like.

The second procedure includes bleaching with a peroxide (common practice in the West), coating with a masking agent (typified by tooth manicure), and laminate veneer technique.

The recent increasing interest in dental health and aesthetic appreciation has shifted the procedure for tooth whitening from "cleaning" to "making teeth look white". However, bleaching with a peroxide is not approved for domestic use because of its complex procedure and danger, although limited bleaching agents are commercially available for dentists. On the other hand, coating with manicure lacks natural appearance and also lacks durability (it easily peels off after eating and drinking). Laminate veneer technique belongs to the dentist's domain. Moreover, it necessitates grinding the surface of healthy teeth, and the ground teeth cannot be restored even though the patient is not satisfied with the results of operation.

For the reasons mentioned above, there has been a demand for improvement in the conventional technique of "making teeth look white". Such improvement should meet requirements for aesthetical appreciation, simple and safe use, no chemical reactions involved, and easy restoration in case of dissatisfaction with results.

Among the conventional reversible (restorable) whitening techniques involving no chemical reactions is coating with manicure made of shellac, vinyl acetate resin, or acrylic resin, as proposed in Japanese Patent Laid-open Nos. Hei 4-82821, Hei 5-58844, Hei 9-100215, Hei 9-202718, and Hei 9-151123. However, these techniques still have room for improvement in color tone and durability.

DISCLOSURE OF INVENTION

It is an object of the present invention to provide a method for making teeth look white, a tooth whitening composition to be used for the method, and a tooth whitening set. The method includes changing the optical properties of the enamel without chemical reactions such as bleaching.

The present inventors have found that teeth can be made to apparently look white by an entirely new method different from conventional ones. This method involves a whitening component that infiltrates into the enamel to replace water therein, thereby changing the optical properties (refractive index, reflectance, and the like) of the enamel without chemical reactions such as bleaching.

The present invention provides a method for reversibly making teeth look white in the presence of water. The method includes causing a tooth whitening component to infiltrate into the enamel through its surface and to remain in the enamel, thereby changing the optical properties of the enamel without chemical reactions so that the enamel looks apparently cloudy and whiter than original. The changeable optical properties of the enamel include refractive index and reflectance. The present invention also provides a tooth whitening composition to be used for the method mentioned above. The composition contains a tooth whitening component such that its liquid component has a refractive index of 1.35 to 1.50 (measured by an Abbe refractometer with sodium D-line at 20° C.). The tooth whitening component is one or more selected from lower alcohols having four or less carbon atoms, glycol having ten or less carbon atoms, polyethylene glycol, glycerin, and diglycerin, with the ratio of the whitening component to water being at least 30/70 by weight.

The present invention also provides a tooth whitening set which includes the tooth whitening composition mentioned above and a tool for its application which is detachably fitted to teeth while holding the tooth whitening composition. The tool for application may be a tape, sheet, film, dental tray, mouth tray, mouth piece, sponge, impression material, packing material, tooth cover conforming to the dentition, or chewing brush conforming to the dentition which has many projections on its surface in contact with teeth, which are all made of a water-insoluble material. It is desirable to use the tool for application when the above-mentioned tooth whitening method is practiced.

BEST MODE FOR CARRYING OUT THE INVENTION

The invention will be described below in more detail.

The tooth whitening method according to the present invention achieves its object because the tooth whitening component remains on the surface of the teeth such that it infiltrates into the enamel to replace water therein, thereby changing the optical properties (refractive index, reflectance, and the like) of the enamel and hence making the enamel apparently look cloudy and white. Therefore, the method is highly safe without chemical reactions involved. After whitening, the treated teeth go back to their original color within several hours because the whitening component, which has infiltrated into the enamel, is gradually replaced by water from saliva. The tooth whitening by the method is reversible and hence is suitable for home care.

The tooth whitening method according to the present invention is effectively practiced by using a tool to be fitted to teeth which holds the composition (in the form of liquid, paste, gel, foam, or powder) containing the tooth whitening component.

According to the present invention, the whitening component contained in the tooth whitening composition should preferably be one or more species selected from lower alcohols having four or less carbon atoms, glycol having ten or less carbon atoms, polyethylene glycol, glycerin, and diglycerin.

No specific restrictions are imposed on the lower alcohol, which is used in the present invention, so long as it has four or less carbon atoms. Its preferred examples include ethanol, isopropyl alcohol, n-propanol, and n-butanol.

No specific restrictions are imposed on the glycol, which is used in the present invention, so long as it has ten or less carbon atoms. Its preferred examples include propylene glycol, diethylene glycol, ethylene glycol, dipropylene glycol, and 1,3-butylene glycol.

The polyethylene glycol used in the present invention should preferably have a molecular weight of 200 to 800, more preferably 200 to 600. With a molecular weight smaller than 200 or larger than 800, it may not produce the whitening effect satisfactorily.

According to the present invention, the tooth whitening composition containing a whitening component is characterized in that it contains a liquid component having a refractive index of 1.35 to 1.50 (measured by Abbe refractometer with sodium D-line at 20° C.). With a refractive index larger than 1.50, the composition will not produce the tooth whitening effect satisfactorily. With a refractive index smaller than 1.35, the composition might produce an unnatural white color.

The whitening component used in the present invention should preferably be in the form of mixture with water such that the ratio (by weight) of whitening component to water is at least 30/70, more preferably at least 40/60 (even as high as 100/0). With a ratio smaller than 30/70, the whitening component may not produce its effect satisfactorily.

According to the present invention, the tooth whitening composition contains the whitening component without specific restrictions except that the amount of the whitening component meets the following condition. The liquid component leaching out of the composition contains the whitening component such that the ratio (by weight) of whitening component to water is 30/70 or more. The amount of the whitening component should preferably be 20 to 100%, particularly 25 to 100% (by weight; % shows "% by weight" hereinafter), of the entire composition.

The tooth whitening composition according to the present invention may be incorporated, in addition to the above-mentioned whitening component, with optional components given below depending on its dosage forms.

For example, the whitening composition may be used in the form of gel or paste, with the help of a gelling agent, so as to facilitate its application to teeth or its adhesion to teeth. Examples of the gelling agent include cellulose derivatives (such as hydroxyethyl cellulose, carboxymethyl cellulose sodium, and methyl cellulose), gums (such as sodium alginate, carrageenan, xanthan gum, tragacanth gum, acacia gum, jellan gum, and native jellan gum), synthetic binders (such as polyvinyl alcohol, sodium polyacrylate, carboxyvinyl polymer, polyvinyl pyrrolidone, and polyethylene oxide), and inorganic binders (such as silica gel, aluminum silica gel, bee gum, and Laponite). They may be used alone or in combination with one another.

Of these examples, hydroxyethyl cellulose, carboxymethyl cellulose sodium, sodium alginate, carrageenan, xanthan gum, native jellan gum, polyvinyl alcohol, and carboxyvinyl polymer are preferable-as the gelling agent because of their good feeling in use (freedom from stickiness and dissolution in the mouth). Particularly desirable are hydroxyethyl cellulose, carboxymethyl cellulose sodium, sodium alginate, carrageenan, xanthan gum, and carboxyvinyl polymer.

The above-mentioned gelling agent should be used in an amount of 0.1 to 15%, particularly 0.5 to 10%, of the total amount of the whitening composition, so that the whitening composition firmly adheres alone to teeth when used in combination with tape, sheet, or tooth cover. With an amount less than specified above, the gelling agent does not produce the desired adhering power, making it difficult for the whitening composition to be used in combination with tape, sheet, or tooth cover. With an excessive amount, the gelling agent might result in an inhomogeneous composition due to incomplete dissolution.

In addition, for the purpose of emulsification and dispersion, the whitening composition may be incorporated with one or more surfactants selected from anionic surfactants, nonionic surfactants, and amphoteric surfactants. Their amount is not specifically restricted; but it is usually 0.1 to 10%, particularly 0.1 to 5%, of the total amount of the composition.

Examples of the anionic surfactants include sodium alkyl sulfate (such as sodium lauryl sulfate, sodium myristyl sulfate, and sodium cetyl sulfate); sodium N-acyl-glutamate (such as sodium N-lauroyl glutamate, and sodium N-acylsarcosine glutamate); sodium N-acylsarcosine (such as sodium N-lauroyl sarcosine and sodium N-myristoyl sarcosine); sodium N-methyl-N-acyltaurin (such as sodium N-lauroyl-methyl-taurin and sodium N-myristoyl-methyl taurin); sodium N-methyl-N-acylalanine, sodium laurylbenzene sulfonate, sodium hydrogenated coconut fatty acid monoglyceride monosulfate, sodium laurylsulfoacetate, sodium a-olefinsulfonate, sodium lauryl POE sulfate, sodium lauryl POE acetate, sodium lauryl POE phosphate, and sodium stearyl POE phosphate.

Examples of the nonionic surfactants include glycerin fatty acid ester (such as monoglyceryl stearate and decaglyceryl laurate), sugar fatty acid ester (such as sucrose fatty acid ester, maltose fatty acid ester, and lactose fatty acid ester); sugar alcohol fatty acid ester (such as maltitol fatty acid ester and lactitol fatty acid ester); polyoxyethylene sorbitan fatty acid ester (such as polyoxyethylene sorbitan monolaurate and polyoxyethylene sorbitan monostearate), polyoxyethylene fatty acid ester (such as polyoxyethylene hardened caster oil), fatty acid ethanolamide (such as mono- or diethanol-amide myristate), sorbitan fatty acid ester, polyoxyethylene higher alcohol ether, polyoxyethylene polyoxypropylene copolymer, and polyoxyethylene polyoxypropylene fatty acid ester.

Examples of the amphoteric surfactants include alkyldimethylaminoacetic acid betaine (such as lauryl dimethylaminoacetic acid betaine), N-alkyldiaminoethylglycine (such as N-laurylaminoethylglycine and N-myristyldiamino-ethylglycine), N-alkyl-N-carboxymethylammonium betaine, and sodium 2-alkyl-1-hydroxyethylimidazoline betaine.

The whitening composition according to the present invention may be further incorporated with one or more adjuvants exemplified below. Enzymes (such as dextranase, mutanase, lysozyme, amylase, protease, lytic enzyme, and superoxide dismutase); metal monofluorophosphate (such as sodium monofluorophosphate and potassium monofluorophosphate), fluorine compounds (such as potassium pyrophosphate, sodium tripolyphosphate, and sodium fluoride), water-soluble polyphosphates (such as sodium metaphosphate), allantoin, dihydrocholestanol, glycyrrhizic acid, glycyrrhetinic acid, ε-amino-caproic acid, tranexamic acid, bisabolol, isopropylmethyl phenol, sodium chloride, triclosan, chlorhexidine salt, cetylpyridinium chloride, benzethonium chloride, benzalkonium chloride, ascorbic acid and salt thereof, tocopherol, and crude drug extracts (such as scutellaria root, phellodendron bark, rosemary, clove, and thyme).

The whitening composition according to the present invention may be incorporated further with a flavor (such as menthol, anethole, carvone, peppermint, and spearmint), preservative (such as benzoic acid and sodium salt thereof and paraben), dye or colorant (such as Red No. 3, Red No. 104, Yellow No. 4, Blue No. 1, Green No. 3, titanium dioxide coated mica, and red iron oxide), and sweetener (such as saccharin sodium, stevioside, glycyrrhizin, and aspartame).

The whitening composition is not specifically restricted in pH so long as it has a pH value harmless to the mouth and human body. Adequate pH values are 5.5 to 9. For the purpose of pH adjustment, the whitening composition may be incorporated with any one of hydrochloric acid, sulfuric acid, nitric acid, citric acid, phosphoric acid, sodium hydroxide, potassium hydroxide, sodium carbonate, sodium citrate, sodium hydrogen citrate, sodium phosphate, and sodium hydrogen phosphate.

As mentioned above, the tooth whitening composition of the present invention should preferably be applied to teeth in concert with a special tool which retains and keeps it in position in contact with teeth. Such a tool prevents the composition from dissolving onto the gum, tongue, and oral mucosa during use. Moreover, it eliminates unpleasant feeling and excess salivation and prevents a dilution of the composition by invasion of saliva and a detachment from teeth by occlusion and chewing. It is not specifically restricted in its material and shape so long as it achieves the above-mentioned object. It may be formed from a water-insoluble material and it may be in the form of tape, sheet, film, dental tray, mouth tray, mouth piece, sponge, impression material, packing material, tooth cover conforming to the dentition, or chewing brush conforming to the dentition which has many projections on its surface in contact with teeth.

The above-mentioned tool should preferably have a thickness of 0.01 to 5 mm so that it does not give uncomfortable feeling when it is placed in the mouth. The thickness of tape, sheet, or film should preferably be 0.01 to 2 mm.

The above-mentioned tool should preferably be formed from a material that gives a pleasant feeling in the mouth and prevents excess salivation during use, thereby permitting the composition to stay in the mouth for a long period of time. Examples of the material include polyethylene, foamed polyethylene, polypropylene, foamed polypropylene, polyester, rayon, pulp, cotton, silk, and paper. They may be used alone or in combination with one another. Preferred examples are polyethylene, foamed polyethylene, polypropylene, foamed polypropylene, polyester, and rayon. The tool may be formed from two kinds of materials. In other words, that side of the tool which comes into contact with the dental mucosa and tongue should preferably be formed from a hydrophilic water-absorbing material, such as cloth or non-woven fabric of rayon, pulp, cotton, silk, or paper. Such a material absorbs saliva, thereby giving a pleasant feeling. That side of the tool holding the whitening composition should preferably be formed from a water-impermeable film of polyethylene, polypropylene, or polyester. Such a film prevents the whitening components from adsorbing to or infiltrating into the tool.

On the other hand, it is desirable to form the tray, mouthpiece, and chewing brush from silicone rubber, natural rubber, or the like of plastic resin or vinyl acetate resin, acrylic resin, or ethylene-vinyl acetate resin of thermoplastic resin, which easily deforms to fit to the user's dentition and tooth shape. The resulting tool firmly sticks to teeth and makes the whitening composition to produce its effect for a long period of time.

In the case where the tooth whitening composition is in the form of liquid or low viscous liquid (which does not firmly stick to teeth), it is possible to cover the inside of the tooth cover or tray with a sponge (or the like made of water-absorbing material such as rayon, cotton, and pulp) impregnated with the composition. The user continuously fixes by bite of the tooth cover or tray so that the composition in a proper amount is applied to his or her teeth.

The frequency and duration of application should be properly selected. Usually, once to six times a day (particularly once to three times a day) and 1 to 120 minutes (particularly 1 to 60 minutes) for one dosage. Application while sleeping is also possible.

EXAMPLE

The invention will be described in more detail with reference to the following examples and comparative examples, which are not intended to restrict the scope thereof. Incidentally, the whitening component used in the following examples all have a refractive index of 1.35 to 1.50.

Example 1 and Comparative Example 1

An experiment was conducted as follows with an extracted human tooth which had previously been examined for L*a*b* values (CIE). The tooth was enclosed in absorbent cotton impregnated with a liquid compound (in 100% concentration) shown below, and the resulting object was allowed to stand at 37° C. for 1 hour in a closed glass bottle. The tooth was examined again for L*a*b* values (CIE). The $\Delta L$ and $\Delta b$ values measured before and after treatment were used to calculate the whiteness ($\Delta|L|+\Delta|b|$) of the tooth, which is a measure of the effect (1).

The tooth which had been processed as mentioned above was again allowed to stand at 37° C. for 1 hour in a closed glass bottle containing 10 ml of water at 37° C. Then, the tooth was examined again for L*a*b* values (CIE). The $\Delta L$ and $\Delta b$ values measured before and after treatment were used to calculate the whiteness ($\Delta|L|+\Delta|b|$) of the tooth, which is a measure of the prolonged effect (2). The results are shown in Table 1.

TABLE 1

|  | Compound | Conc. | Effect (1)* | Effect (2)** | Result*** |
|---|---|---|---|---|---|
| Example 1 | Isopropyl alcohol | 100% | 15.8 | 8.3 | ⊚ |
|  | 1,3-butylene glycol | 100% | 11.3 | 5.6 | ⊚ |
|  | PEG #200 | 100% | 12.5 | 4.8 | ⊚ |
|  | PEG #300 | 100% | 10.7 | 3.7 | ⊚ |
|  | Ethanol | 100% | 12.8 | 3.0 | ⊚ |
|  | Propylene glycol | 100% | 8.4 | 2.8 | ⊚ |
|  | Diethylene glycol | 100% | 14.4 | 2.6 | ⊚ |
|  | Ethylene glycol | 100% | 9.3 | 2.6 | ⊚ |
|  | Dipropylene glycol | 100% | 8.6 | 1.6 | ⊚ |
|  | PEG #400 | 100% | 8.1 | 1.5 | ⊚ |
|  | PEG #600 | 100% | 12.0 | 0.6 | ○ |
| Comparative Example 1 | Water |  | 0.0 | 0.0 | X |

*Measured immediately after immersion in the compound for 1 hour.
**Measured after immersion in water for 1 hour.
***⊚ denotes a significant prolonged effect with a value larger than 1, and ○ denotes a prolonged effect with a value larger than 0.5.

Example 2 and Comparative Example 2

An experiment was conducted as follows with an extracted human tooth which had previously been examined for L*a*b* values (CIE). The tooth was enclosed in a sheet of non-woven fabric of PP coated with a gel composed of 50% of the whitening compound specified below, 0.5% of jellan gum, and 49.5% of water, and the resulting object was allowed to stand at 37° C. for 1 hour in a closed glass bottle. The tooth was examined again for L*a*b* values (CIE). The $\Delta L$ and $\Delta b$ values measured before and after treatment were used to calculate the whiteness (Δ|L|+Δ|b|) of the tooth, which is a measure of the effect (3).

The tooth which had been processed as mentioned above was again allowed to stand at 37° C. for 1 hour in a closed glass bottle containing 10 ml of water at 37° C. Then, the tooth was examined again for L*a*b* values (CIE). The ΔL and Δb values measured before and after treatment were used to calculate the whiteness (Δ|L|+Δ|b|) of the tooth, which is a measure of the prolonged effect (4). The results are shown in Table 2.

TABLE 2

|  | Compound | Conc. | Effect (3)* | Effect (4)** | Result*** |
|---|---|---|---|---|---|
| Example 2 | Dipropylene glycol | 50% | 1.8 | 2.3 | ◎ |
|  | Ethanol | 50% | 1.5 | 1.9 | ◎ |
|  | Diethylene glycol | 50% | 1.3 | 1.1 | ◎ |
|  | Propylene glycol | 50% | 1.0 | 1.0 | ◎ |
|  | PEG #200 | 50% | 0.6 | 0.9 | ○ |
|  | PEG #300 | 50% | 1.8 | 0.8 | ○ |
|  | PEG #600 | 50% | 0.7 | 0.8 | ○ |
|  | Ethylene glycol | 50% | 1.6 | 0.7 | ○ |
|  | PEG #400 | 50% | 0.7 | 0.6 | ○ |
|  | Isopropyl alcohol | 50% | 1.1 | 0.5 | ○ |
|  | 1,3-butylene glycol | 50% | 0.9 | 0.5 | ○ |
| Comparative Example 2 | Water |  | 0.0 | 0.0 | X |

*Measured immediately after immersion in the compound for 1 hour.
**Measured after immersion in water for 1 hour.
*** ◎ denotes a significant prolonged effect with a value larger than 1, and ○ denotes a prolonged effect with a value larger than 0.5.

Example 3

Foamed polyethylene tape (0.1 mm thick) with an adhesive layer of the following paste composition 1. The tape as such is stuck to the teeth.

| [Whitening composition 1 (in paste form)] | |
|---|---|
| Glycerin | 30.0 |
| Polyethylene glycol #400 | 3.0 |
| Sodium lauryl sulfate | 2.0 |
| Hydroxyethyl cellulose | 1.5 |
| Sodium alginate | 1.5 |
| Methyl benzoate | 0.5 |
| Flavor | 1.0 |
| Saccharin sodium | 0.1 |
| Pure water | balance |
| Total | 100.0% |

Example 4

Rayon non-woven fabric (1 mm thick) coated with the following gel composition 2. The sheet as such is stuck to the teeth.

| [Whitening composition 2 (in gel form)] | |
|---|---|
| Ethanol | 10.0 |
| Glycerin | 20.0 |
| Sorbitol | 20.0 |
| Silicic anhydride | 10.0 |
| Sodium carboxymethyl cellulose | 2.0 |
| Sodium N-lauroyl sarcosinate | 1.0 |
| Sodium monofluorophosphate | 0.7 |
| Sodium benzoate | 0.5 |
| Methyl benzoate | 0.1 |
| Flavor | 1.0 |
| Saccharin sodium | 0.1 |
| Pure water | balance |
| Total | 100.0% |

Example 5

Polyethylene film (0.01 mm thick) coated with the following gel composition 3. The film as such is stuck to the teeth.

| [Whitening composition 3 (in gel form)] | |
|---|---|
| Isopropanol | 10.0 |
| Propylene glycol | 30.0 |
| Sorbitol | 10.0 |
| Calcium hydrogen phosphate | 10.0 |
| Carrageenan | 3.0 |
| Sodium monofluorophosphate | 0.7 |
| Cetyl pyridinium chloride | 0.01 |
| Flavor | 1.2 |
| Saccharin sodium | 0.1 |
| Pure water | balance |
| Total | 100.0% |

Example 6

Polypropylene film (0.05 mm thick) coated with the following gel composition 4. The film as such is stuck to the teeth.

| [Whitening composition 4 (in gel form)] | |
|---|---|
| Diethylene glycol | 40.0 |
| Xanthan gum | 2.0 |
| Carrageenan | 1.0 |
| Sodium lauryl sulfate | 1.0 |
| Sodium N-lauroyl sarcosinate | 0.5 |
| Diethanolamide myristate | 0.5 |
| Chlorhexidine gluconate | 0.01 |
| Flavor | 1.5 |
| Saccharin sodium | 0.1 |
| Pure water | balance |
| Total | 100.0% |

Example 7

Polyester tape (0.05 mm thick) with an adhesive layer of the following gel composition 5. The tape as such is stuck to the teeth.

| [Whitening composition 5 (in gel form)] | |
|---|---|
| Ethanol | 30.0 |
| n-Propanol | 20.0 |

| [Whitening composition 5 (in gel form)] | |
|---|---|
| Glycerin | 20.0 |
| Hydroxyethyl cellulose | 7.0 |
| Sodium lauryl sulfate | 2.0 |
| Polyvinyl pyrrolidone | 1.0 |
| Flavor | 1.0 |
| Saccharin sodium | 0.2 |
| Pure water | balance |
| Total | 100.0% |

Example 8

Sheet of mixed non-woven fabric of polypropylene and rayon (2.0 mm thick) coated with the following gel composition 6. The sheet as such is stuck to the teeth.

| [Whitening composition 6 (in gel form)] | |
|---|---|
| Ethanol | 15.0 |
| Ethylene glycol | 10.0 |
| Polyethylene glycol #200 | 10.0 |
| Sorbitol | 10.0 |
| Sodium carboxymethyl cellulose | 3.0 |
| Carrageenan | 1.0 |
| Dextranase | 0.05 |
| Flavor | 1.0 |
| Saccharin sodium | 0.1 |
| Pure water | balance |
| Total | 100.0% |

Example 9

Sheet of rayon non-woven fabric (0.5 mm thick) impregnated with the following liquid composition 7. The sheet as such is stuck to the teeth.

| [Whitening composition 7 (in liquid form)] | |
|---|---|
| Glycerin | 50.0 |
| 1,3-butylene glycol | 40.0 |
| Polyoxyethylene (60 mol) hardened castor oil | 1.0 |
| Xanthan gum | 1.0 |
| Sodium fluoride | 0.2 |
| Flavor | 1.0 |
| Saccharin sodium | 0.1 |
| Pure water | balance |
| Total | 100.0% |

Example 10

Tooth cover composed of PP/PE film/rayon+PP three-layered non-woven fabric (3.0 mm thick) impregnated with the following liquid composition 8. The tooth cover as such is fitted to the teeth.

| [Whitening composition 8 (in liquid form)] | |
|---|---|
| Ethylene glycol | 80.0 |
| Polyoxyethylene polyoxypropylene glycol | 1.0 |
| Xanthan gum | 1.0 |
| Sodium triphosphate | 1.0 |
| Cetylpyridinium chloride | 0.05 |
| Flavor | 1.0 |
| Saccharin sodium | 0.1 |
| Pure water | balance |
| Total | 100.0% |

Example 11

A combination of polyethylene film (0.1 mm thick) and the following paste composition 9. The paste composition is applied to the teeth and then covered with the film.

| [Whitening composition 9 (in paste form)] | |
|---|---|
| Dipropylene glycol | 50.0 |
| Sorbitol | 20.0 |
| Sodium carboxymethyl cellulose | 2.0 |
| Hydroxyethyl cellulose | 1.0 |
| Sodium lauryl sulfate | 1.0 |
| Triclosan | 0.1 |
| Flavor | 1.0 |
| Saccharin sodium | 0.1 |
| Pure water | balance |
| Total | 100.0% |

Example 12

A sponge (having cuts conforming to the dentition) impregnated with the following liquid composition 10. The sponge as such is fitted to the teeth or chewed.

| [Whitening composition 10 (in liquid form)] | |
|---|---|
| Glycerin | 95.0 |
| Sodium carboxymethyl cellulose | 0.5 |
| Flavor | 0.5 |
| Saccharin sodium | 0.1 |
| Pure water | balance |
| Total | 100.0% |

Example 13

A combination of tooth packing material (made of water-insoluble acrylate) and the following paste composition 11. The paste composition is applied to the teeth and then it is further coated with the packing material.

| [Whitening composition 11 (in paste form)] | |
|---|---|
| Ethanol | 5.0 |
| Sorbitol | 20.0 |
| Polyethylene glycol #600 | 25.0 |
| Sodium lauryl sulfate | 2.0 |
| Hydroxyethyl cellulose | 2.0 |

-continued

[Whitening composition 11 (in paste form)]

| | |
|---|---|
| Sodium alginate | 1.0 |
| Polyoxyethylene polyoxypropylene glycol | 0.5 |
| Flavor | 1.5 |
| Saccharin sodium | 0.2 |
| Pure water | balance |
| Total | 100.0% |

Example 14

A combination of mouth tray (with cotton balls arranged inside) and the following liquid composition 12. The cotton balls are impregnated with the liquid composition and the mouth tray is fixed.

[Whitening composition 12 (in liquid form)]

| | |
|---|---|
| Ethanol | 40.0 |
| Isopropyl alcohol | 30.0 |
| Polyethylene glycol #400 | 30.0 |
| Total | 100.0% |

Example 15

A combination of mouth tray (made of silicone rubber) and the following foamy composition 13. The foamy composition is cast up on the mouth tray and the mouth tray is fixed.

[Whitening composition 13 (in foamy form)]

| | |
|---|---|
| Ethanol | 30.0 |
| Sodium lauryl sulfate | 3.0 |
| Diethanolamide myristate | 1.0 |
| Carboxyvinyl polymer | 0.5 |
| Sodium monofluorophosphate | 0.7 |
| Flavor | 1.0 |
| Stevioside | 0.5 |
| Pure water | balance |
| Total | 100.0% |

Example 16

A combination of mouth tray conforming to the individual dentition (made of thermoplastic ethylene-vinyl acetate copolymer) and the following toothpaste-like composition 14. The mouth tray is filled with the toothpaste-like composition and the mouth tray is chewed.

[Whitening composition 14 (in toothpaste-like form)]

| | |
|---|---|
| Propylene glycol | 30.0 |
| Calcium carbonate | 20.0 |
| Silicic anhydride | 5.0 |
| Sodium lauryl sulfate | 1.0 |
| Sodium carboxymethyl cellulose | 1.0 |
| Carrageenan | 1.0 |
| Sodium monofluorophosphate | 0.7 |

-continued

[Whitening composition 14 (in toothpaste-like form)]

| | |
|---|---|
| Sodium N-lauroyl sarcosinate | 0.5 |
| Methyl benzoate | 0.5 |
| Flavor | 1.0 |
| Saccharin sodium | 0.1 |
| Pure water | balance |
| Total | 100.0% |

Example 17

A chewing brush of natural rubber in which embedded the following gel composition 15. The chewing brush as such is chewed.

[Whitening composition 15 (in gel form)]

| | |
|---|---|
| Glycerin | 30.0 |
| Silicic anhydride | 10.0 |
| Polyoxyethylene polyoxypropylene glycol | 10.0 |
| Carboxyvinyl polymer | 2.0 |
| Flavor | 0.5 |
| Saccharin sodium | 0.1 |
| Pure water | balance |
| Total | 100.0% |

The present invention provides a method for making teeth apparently look white by causing a tooth whitening component to infiltrate into the tooth enamel and to stay therein so that the whitening component changes the optical properties (refractive index, reflectance, and the like) of the enamel. The treated teeth restore their original color in the presence of water.

The invention claimed is:

1. A method for reversibly making teeth look white in the presence of water without chemical bleaching reaction due to a peroxide,
    said method comprising applying a tape, sheet or film having a gel or paste composition comprising a gelling agent, a tooth whitening component and water coated thereon to teeth for 1 to 120 minutes so that the composition is stuck to teeth and covered by the tape, sheet or film thereby preventing the composition from being diluted by invasion of saliva,
    said tooth whitening component being one or more selected from the group consisting of lower alcohols having four or less carbon atoms, glycols having ten or less carbon atoms, polyethylene glycols, glycerin, and diglycerin, with the ratio of the tooth whitening component to water being no smaller than 50/49.5, said tooth whitening composition being free of a bleaching agent including a peroxide,
    wherein when said tape, sheet or film is applied, said tooth whitening component infiltrates into an enamel through its surface and to remain in the enamel, thereby changing optical properties of the enamel without chemical reactions so that the enamel looks apparently cloudy and whiter than original, and
    after whitening, said one or more tooth whitening components in the enamel is replaced by water from saliva, thereby going back to the original color of the enamel reversibly.

2. The method of claim 1, wherein the tooth whitening component is selected from the group consisting of glycol having ten or less carbon atoms and polyethylene glycols.

3. The method of claim 1, wherein with the ratio of the tooth whitening component to water is no smaller than 73/27.

4. The method of claim 1, wherein the ratio of the tooth whitening component to water is no smaller than 83/17.

5. The method of claim 1, wherein the ratio of the tooth whitening component to water is 100/0.

6. The method of claim 5, wherein the tooth whitening component is selected from the group consisting of glycol having ten or less carbon atoms and polyethylene glycols.

7. The method of claim 1, wherein the tooth whitening composition consists essentially of a gelling agent, a tooth whitening component selected from the group consisting of lower alcohols having four or less carbon atoms, glycols having ten or less carbon atoms, polyethylene glycols, glycerin and diglycerin, and water, with the ratio of the tooth whitening component to water being no smaller than 50/49.5.

8. The method of claim 7, wherein the ratio of the tooth whitening component to water being no smaller than 73/27.

9. The method of claim 7, wherein the ratio of the tooth whitening component to water is no smaller than 83/17.

10. The method of claim 7, wherein the ratio of the tooth whitening component to water is 100/0.

11. A tooth whitening set for reversible making tooth look white in the presence of water without chemical bleaching reactions due to a peroxide, said tooth whitening set comprising a tape, sheet or film and a gel or paste composition coated on the tape, sheet or film and comprising a gelling agent, a tooth whitening component selected from the group consisting of lower alcohols having four or less carbon atoms, glycols having ten or less carbon atoms, polyethylene glycols, glycerin and diglycerin, and water, the ratio of the tooth whitening component to water being no smaller than 50/49.5, said tooth whitening composition being free of a bleaching agent including a peroxide, said tape, sheet or film retaining and keeping the composition in position in contact with teeth for 1 to 120 minutes by covering the composition and preventing the dilution of the composition by invasion of saliva to ensure that the tooth whitening component infiltrates into an enamel though its surface and to remain in the enamel, thereby changing optical properties of the enamel without chemical reactions so that the enamel looks apparently cloudy and whiter than original.

12. The set of claim 11, wherein the tooth whitening component is selected from the group consisting of glycol having ten or less carbon atoms and polyethylene glycols.

13. The set of claim 11, wherein the ratio of the tooth whitening component to water is no smaller than 73/27.

14. The set of claim 11, wherein the ratio of the tooth whitening component to water is no smaller than 83/17.

15. The set of claim 11, wherein the ratio of the tooth whitening component to water is 100/0.

16. The set of claim 15, wherein the tooth whitening component is selected from the group consisting of glycol having ten or less carbon atoms and polyethylene glycols.

17. The set of claim 11, wherein the tooth whitening composition consists essentially of a gelling agent, a tooth whitening component selected from the group consisting of lower alcohols having four or less carbon atoms, glycols having ten or less carbon atoms, polyethylene glycols, glycerin and diglycerin, and water, with the ratio of the tooth whitening component to water being no smaller than 50/49.5.

18. The set of claim 17, wherein the ratio of the tooth whitening component to water being no smaller than 73/27.

19. The set of claim 17, wherein the ratio of the tooth whitening component to water is no smaller than 83/17.

20. The set of claim 17, wherein the ratio of the tooth whitening component to water is 100/0.

* * * * *

UNITED STATES PATENT AND TRADEMARK OFFICE
CERTIFICATE OF CORRECTION

PATENT NO. : 7,648,363 B2  Page 1 of 1
APPLICATION NO. : 10/491191
DATED : January 19, 2010
INVENTOR(S) : Oniki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 590 days.

Signed and Sealed this

Sixteenth Day of November, 2010

David J. Kappos
*Director of the United States Patent and Trademark Office*